(12) United States Patent
Ellis et al.

(10) Patent No.: US 8,569,070 B2
(45) Date of Patent: Oct. 29, 2013

(54) CONNECTION ASSEMBLY FOR ULTRA HIGH PRESSURE LIQUID CHROMATOGRAPHY

(75) Inventors: Scott J. Ellis, Anacortes, WA (US); Eric Beemer, Bellingham, WA (US); Nathaniel Nienhuis, Oak Harbor, WA (US); Craig W. Graham, Anacortes, WA (US); Troy N. Sanders, Oak Harbor, WA (US)

(73) Assignee: IDEX Health & Science LLC, Oak Harbor, WA (US)

( * ) Notice: Subject to any disclaimer, the term of this patent is extended or adjusted under 35 U.S.C. 154(b) by 524 days.

(21) Appl. No.: 12/838,032

(22) Filed: Jul. 16, 2010

(65) Prior Publication Data

US 2012/0014848 A1   Jan. 19, 2012

(51) Int. Cl.
    *G01N 30/02* (2006.01)
(52) U.S. Cl.
    USPC ........... 436/161; 436/183; 422/70; 422/89; 422/544; 422/545; 422/546; 210/198.2; 73/23.35; 73/23.42; 73/61.52; 73/61.56; 96/106
(58) Field of Classification Search
    USPC .......... 422/70, 89, 544–546; 73/23.35–23.42, 73/61.52–61.58; 210/198.2; 96/101–107; 436/161, 183
    See application file for complete search history.

(56) References Cited

U.S. PATENT DOCUMENTS

| | | | |
|---|---|---|---|
| 5,472,598 A | 12/1995 | Schick | |
| 5,525,303 A | 6/1996 | Ford et al. | |
| 5,601,785 A | 2/1997 | Higdon | |
| 5,651,885 A | 7/1997 | Schick | |
| 5,730,943 A | 3/1998 | Ford et al. | |
| 6,095,572 A | 8/2000 | Ford et al. | |
| 7,311,502 B2 | 12/2007 | Gerhardt et al. | |
| 2005/0097763 A1* | 5/2005 | Williams et al. | 33/501.45 |
| 2005/0269264 A1 | 12/2005 | Fermier et al. | |
| 2007/0283746 A1 | 12/2007 | Gerhardt et al. | |
| 2008/0309076 A1* | 12/2008 | Cormier | 285/256 |
| 2009/0295156 A1* | 12/2009 | Ford et al. | 285/384 |
| 2010/0224546 A1* | 9/2010 | Ellis et al. | 210/232 |

FOREIGN PATENT DOCUMENTS

| | | |
|---|---|---|
| WO | WO 2006/083597 A2 | 8/2006 |
| WO | WO 2010/102225 A1 | 9/2010 |

OTHER PUBLICATIONS

International Search Report and Written Opinion of the International Searching Authority, International Patent Application No. PCT/US2011/044392, Oct. 19, 2012.

* cited by examiner

*Primary Examiner* — Jan Ludlow
(74) *Attorney, Agent, or Firm* — Vinson & Elkins LLP (57) ABSTRACT

A fitting assembly having a nut, a ferrule, and a ferrule tip that may be assembled by an operator. The fitting assembly includes a nut with first and second ends, with the second end adapted to receive the first end of a ferrule, and a ferrule tip with a first end having an externally tapered portion adapted to abut the second end of the ferrule and a second end adapted to be received in a component or fitting of a liquid chromatography system. The nut, ferrule and ferrule tip of the fitting assembly have passageways therethrough for receiving and removably holding tubing.

29 Claims, 6 Drawing Sheets

CONNECTION ASSEMBLY FOR ULTRA HIGH PRESSURE LIQUID CHROMATOGRAPHY

CROSS-REFERENCE TO RELATED APPLICATION

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

1. Field of the Invention

This invention relates generally to an assembly for use in connecting components of liquid chromatography and other analytical systems, and relates more particularly to an assembly well-suited for allowing quick connections and disconnections of components in liquid chromatography systems used in ultra-high pressure liquid chromatography.

2. Description of the Related Art

Liquid chromatography (LC) is a well-known technique for separating the constituent elements in a given sample. In a conventional LC system, a liquid solvent (referred to as the "mobile phase") is introduced from a reservoir and is pumped through the LC system. The mobile phase exits the pump under pressure. The mobile phase then travels via tubing to a sample injection valve. As the name suggests, the sample injection valve allows an operator to inject a sample into the LC system, where the sample will be carried along with the mobile phase.

In a conventional LC system, the sample and mobile phase pass through one or more filters and often a guard column before coming to the column. A typical column usually consists of a piece of steel tubing which has been packed with a "packing" material. The "packing" consists of the particulate material "packed" inside the column. It usually consists of silica- or polymer-based particles, which are often chemically bonded with a chemical functionality. When the sample is carried through the column (along with the mobile phase), the various components (solutes) in the sample migrate through the packing within the column at different rates (i.e., there is differential migration of the solutes). In other words, the various components in a sample will move through the column at different rates. Because of the different rates of movement, the components gradually separate as they move through the column. Differential migration is affected by factors such as the composition of the mobile phase, the composition of the stationary phase (i.e., the material with which the column is "packed"), and the temperature at which the separation takes place. Thus, such factors will influence the separation of the sample's various components.

Once the sample (with its components now separated) leaves the column, it flows with the mobile phase past a detector. The detector detects the presence of specific molecules or compounds. Two general types of detectors are used in LC applications. One type measures a change in some overall physical property of the mobile phase and the sample (such as their refractive index). The other type measures only some property of the sample (such as the absorption of ultraviolet radiation). In essence, a typical detector in a LC system can measure and provide an output in terms of mass per unit of volume (such as grams per milliliter) or mass per unit of time (such as grams per second) of the sample's components. From such an output signal, a "chromatogram" can be provided; the chromatogram can then be used by an operator to determine the chemical components present in the sample.

In addition to the above components, a LC system will often include filters, check valves, a guard column, or the like in order to prevent contamination of the sample or damage to the LC system. For example, an inlet solvent filter may be used to filter out particles from the solvent (or mobile phase) before it reaches the pump. A guard column is often placed before the analytical or preparative column; i.e., the primary column. The purpose of such a guard column is to "guard" the primary column by absorbing unwanted sample components that might otherwise bind irreversibly to the analytical or preparative column.

In practice, various components in an LC system may be connected by an operator to perform a given task. For example, an operator will select an appropriate mobile phase and column, then connect a supply of the selected mobile phase and a selected column to the LC system before operation. In order to be suitable for high performance liquid chromatography (HPLC) applications, each connection must be able to withstand the typical operating pressures of the HPLC system. If the connection is too weak, it may leak. Because the types of solvents that are sometimes used as the mobile phase are often toxic and because it is often expensive to obtain and/or prepare many samples for use, any such connection failure is a serious concern.

It is fairly common for an operator to disconnect a column (or other component) from a LC system and then connect a different column (or other component) in its place after one test has finished and before the next begins. Given the importance of leak-proof connections, especially in HPLC applications, the operator must take time to be sure the connection is sufficient. Replacing a column (or other component) may occur several times in a day. Moreover, the time involved in disconnecting and then connecting a column (or other component) is unproductive because the LC system is not in use and the operator is engaged in plumbing the system instead of preparing samples or other more productive activities. Hence, the replacement of a column in a conventional LC system involves a great deal of wasted time and inefficiencies.

Given concerns about the need for leak-free connections, conventional connections have been made with stainless steel tubing and stainless steel end fittings. More recently, however, it has been realized that the use of stainless steel components in a LC system have potential drawbacks in situations involving biological samples. For example, the components in a sample may attach themselves to the wall of stainless steel tubing. This presents problems because the detector's measurements (and thus the chromatogram) of a given sample may not accurately reflect the sample if some of the sample's components or ions remain in the tubing and do not pass the detector. Perhaps of even greater concern, however, is the fact that ions from the stainless steel tubing may detach from the tubing and flow past the detector, thus leading to potentially erroneous results. Hence, there is a need for "biocompatible" connections through the use of a material which is chemically inert with respect to such "biological" samples and the mobile phase used with such samples so that ions will not be released by the tubing and thus contaminate the sample.

In many applications using selector/injector valves to direct fluid flows, and in particular in liquid and gas chromatography, the volume of fluids is small. This is particularly true when liquid or gas chromatography is being used as an analytical method as opposed to a preparative method. Such methods often use capillary columns and are generally referred to as capillary chromatography. In capillary chromatography, both gas phase and liquid phase, it is often desired to minimize the internal volume of the selector or injector valve. One reason for this is that a valve having a large volume will contain a relatively large volume of liquid, and when a sample is injected into the valve the sample will be diluted, decreasing the resolution and sensitivity of the analytical method.

Micro-fluidic analytical processes also involve small sample sizes. As used herein, sample volumes considered to involve micro-fluidic techniques can range from as low as volumes of only several picoliters or so, up to volumes of several milliliters or so, whereas more traditional LC techniques, for example, historically often involved samples of about one microliter to about 100 milliliters in volume. Thus, the micro-fluidic techniques described herein involve volumes one or more orders of magnitude smaller in size than traditional LC techniques. Micro-fluidic techniques can also be expressed as those involving fluid flow rates of about 0.5 ml/minute or less.

Most conventional HPLC systems include pumps which can generate relatively high pressures of up to around 5,000 psi to 6,000 psi or so. In many situations, an operator can obtain successful results by operating a LC system at "low" pressures of anywhere from just a few psi or so up to 1,000 psi or so. More often than not, however, an operator will find it desirable to operate a LC system at relatively "higher" pressures of over 1,000 psi.

Another, relatively newer liquid chromatography form is Ultra High Performance Liquid Chromatography (UHPLC) in which system pressure extends upward to 1400 bar or 20,000 psi. Both HPLC and UHPLC are examples of analytical instrumentation that utilize fluid transfer at elevated pressures. For example, in U.S. Patent Publication No. US 2007/0283746 A1, published on Dec. 13, 2007 and titled "Sample Injector System for Liquid Chromatography," an injection system is described for use with UHPLC applications, which are said to involve pressures in the range from 20,000 psi to 120,000 psi. In U.S. Pat. No. 7,311,502, issued on Dec. 25, 2007 to Gerhardt, et al., and titled "Method for Using a Hydraulic Amplifier Pump in Ultrahigh Pressure Liquid Chromatography," the use of a hydraulic amplifier is described for use in UHPLC systems involving pressures in excess of 25,000 psi. In U.S. Patent Publication No. US 2005/0269264 A1, published on Dec. 8, 2005 and titled "Chromatography System with Gradient Storage and Method for Operating the Same," a system for performing UHPLC is disclosed, with UHPLC described as involving pressures above 5,000 psi (and up to 60,000 psi). Applicants hereby incorporate by reference as if fully set forth herein U.S. Pat. No. 7,311,502 and US Patent Publications Nos. US 2007/0283746 A1 and US 2005/0269264 A1.

As noted, liquid chromatography (as well as other analytical) systems, including HPLC or UHPLC systems, typically include several components. For example, such a system may include a pump; an injection valve or autosampler for injecting the analyte; a precolumn filter to remove particulate matter in the analyte solution that might clog the column; a packed bed to retain irreversibly adsorbed chemical material; the HPLC column itself; and a detector that analyzes the carrier fluid as it leaves the column. These various components may typically be connected by a miniature fluid conduit, or tubing, such as metallic or polymeric tubing, usually having an internal diameter of 0.003 to 0.040 inch.

All of these various components and lengths of tubing are typically interconnected by threaded fittings. Fittings for connecting various LC system components and lengths of tubing are disclosed in prior patents, for example, U.S. Pat. Nos. 5,525,303; 5,730,943; and 6,095,572, the disclosures of which are herein all incorporated by reference as if fully set forth herein. Often, a first internally threaded fitting seals to a first component with a ferrule or similar sealing device. The first fitting is threadedly connected through multiple turns by hand or by use of a wrench or wrenches to a second fitting having a corresponding external fitting, which is in turn sealed to a second component by a ferrule or other seal. Disconnecting these fittings for component replacement, maintenance, or reconfiguration often requires the use of a wrench or wrenches to unthread the fittings. Although a wrench or wrenches may be used, other tools such as pliers or other gripping and holding tools are sometimes used. In addition, the use of such approaches to connect components of an UHPLC system often results in deformation or swaging of a ferrule used to provide a leak proof seal of tubing to a fitting or component. This often means that the ferrule and tubing connection, once made, cannot be reused without a risk of introducing dead volumes into the system. In addition, such approaches may involve crushing or deformation of the inner diameter of the tubing, which may adversely affect the flow characteristics and the pressures of the fluid within the tubing. While hand-tightened threaded fittings eliminate the need for wrenches or other tools, these fittings typically can not stand up to the extreme pressures of HPLC or UHPLC.

Another approach to provide a connection in an UHPLC system involves providing a fitting assembly that uses a combination of components, including two separate ferrules. Such an approach is considered undesirable because by requiring two places for the ferrules to provide leak proof seals, it provides two places where the fluid to be analyzed may leak, as well as where dead volumes may be provided. In addition, this approach involves the use of additional components, which can cost more and also increase the time and effect to assemble them to make a connection or disassemble them when disconnecting tubing from a component or other fitting assembly.

It will be understood by those skilled in the art that, as used herein, the term "LC system" is intended in its broad sense to include all apparatus and components in a system used in connection with liquid chromatography, whether made of only a few simple components or made of numerous, sophisticated components which are computer controlled or the like. Those skilled in the art will also appreciate that an LC system is one type of an analytical instrument (AI) system. For example, gas chromatography is similar in many respects to liquid chromatography, but obviously involves a gas sample to be analyzed. Although the following discussion focuses on liquid chromatography, those skilled in the art will appreciate that much of what is said also has application to other types of AI systems and methods.

Therefore, it is an object of the present invention to provide a mechanism allowing an operator to quickly disconnect or connect a component of an UHPLC system.

It is another object of the present invention to provide a mechanism to reduce inefficiency and wasted time in connecting or disconnecting a component of an UHPLC system.

It is yet another object of the present invention to provide a mechanism to allow an operator to quickly replace a component of an UHPLC system.

It is yet another object of the present invention to provide a mechanism to allow an operator to quickly and easily achieve a leak-free connection of a component of an UHPLC system.

It is still another object of the present invention to provide a mechanism to minimize the risk of leakage or damage to the tubing of an UHPLC system.

It is still another object of the present invention to provide a biocompatible assembly to allow an operator to quickly and easily achieve a biocompatible connection of a component of an UHPLC system.

The above and other advantages of the present invention will become readily apparent to those skilled in the art from the following detailed description of the present invention, and from the attached drawings, which are briefly described below.

SUMMARY OF THE INVENTION

In a first embodiment of the invention, a fitting assembly is provided that is well-suited for use in liquid chromatography systems, and is particularly well-suited for use in high pressure liquid chromatography and ultra high pressure liquid chromatography. In this embodiment, the fitting assembly includes a nut with two ends and a passageway therethrough, a ferrule having a passageway therethrough, and a ferrule tip having first and second ends and having a passageway therethrough. The passageways through the nut, ferrule, and ferrule tip are adapted to receive and removably hold tubing in this embodiment.

In one embodiment, the present disclosure provides a fitting assembly for use in a liquid chromatography or analytical instrument system, comprising a nut having a first end and a second end, and having a passageway therethrough, wherein the passageway has an internally tapered portion and a lip proximal to the second end of the nut, and wherein the second end of the nut has an externally threaded portion, a ferrule having a first externally tapered end and a second end and having a passageway therethrough, wherein the first externally tapered end of the ferrule is adapted to securely engage with the tapered portion of the passageway in the nut, and a ferrule tip having a first externally tapered end, a central portion, and a second externally tapered end, wherein the first externally tapered end and the central portion define a first lip and the second externally tapered end and the central portion define a second lip, and wherein the first end of the ferrule tip is adapted to abut with the second end of the ferrule within the passageway of the nut, and said first lip of said ferrule tip securely engages said lip of said nut. As used herein, the terms "securely engage" and "securely engages" means that the referenced portions or pieces remain engaged during normal operating conditions. Thus, upon assembly the fitting assembly acts as a "one piece" fitting. The ferrule and ferrule tip are adapted to rotate independently of each other, and the ferrule tip is further adapted to rotate independently of the nut. Thus, the ferrule tip does not transfer tortional loading during the tightening of the nut. This generates more thrust with less torque on the fitting.

The present disclosure further provides a method of connecting tubing in a liquid chromatography or analytical instrument system comprising connecting a fitting assembly comprising a tube extending therethrough to a port, fitting or component of the liquid chromatography system, wherein the fitting assembly comprises a nut having a first end and a second end, and having a passageway therethrough, wherein the passageway has an internally tapered portion and a lip proximal to the second end of the nut, and wherein the second end of the nut has an externally threaded portion, a ferrule having a first externally tapered end and a second end and having a passageway therethrough, wherein the first externally tapered end of the ferrule is adapted to securely engage with the tapered portion of the passageway in the nut, and a ferrule tip having a first externally tapered end, a central portion, and a second externally tapered end, wherein the first externally tapered end and the central portion define a first lip and the second externally tapered end and the central portion define a second lip, and wherein the first end of the ferrule tip is adapted to abut with the second end of the ferrule within the passageway of the nut, and said first lip of said ferrule tip securely engages said lip of said nut, wherein the port, fitting or component of the liquid chromatography or analytical instrument system comprises a first end having an internally threaded portion and an internally tapered portion, and wherein the internally threaded portion of the port, fitting or component of the liquid chromatography or analytical instrument system is adapted to securely engage with the externally threaded portion of the nut, and wherein the internally tapered portion of the port, fitting or component of the liquid chromatography or analytical instrument system is adapted to receive and hold the second externally tapered end of the ferrule tip.

In still another embodiment, a method of assembling a fitting assembly is provided, by which an operator can easily connect tubing to a port, component or fitting of a liquid chromatography (LC) or other analytical instrument (AI) system. In one embodiment, an operator can insert tubing through the passageways of a nut, a ferrule, and a ferrule tip, such as those described above and in more detail below. In certain aspects the fitting assembly is provided to the operator as a pre-assembled unit, while in other aspects the operator assembles the nut, ferrule, and ferrule tip of the fitting assembly prior to use. In still other aspects, the operator can assemble the components of the fitting assembly during the insertion of the tubing through the passageways of the nut, ferrule, and ferrule tip, prior to connection to a port, component or fitting of a LC or AI system. Upon assembly the fitting assembly acts as a one piece fitting. The ferrule tip remains attached to the nut upon assembly, and does not become disengaged in the port, component, or fitting of the LC or AI system, or need to be handled separately. The operator can then engage the externally threaded portion of the nut of the fitting assembly with an internally threaded portion of a port, component or fitting of a LC or other AI system, and then rotate the fitting assembly (by rotating the nut head of the nut) and the port, component or fitting relative to one another, such as by rotating the fitting assembly in a clockwise motion when viewed from the first end of the nut of the fitting assembly. Alternatively, the operator can turn the port, component or fitting relative to the fitting assembly, or turn both the fitting assembly and the port, component or fitting relative to each other. By turning the fitting assembly and the port, component or fitting relative to one another, the threaded external portion of the nut of the fitting assembly engages with the internal threaded portion of the port, component or fitting, further pushing the first end of the ferrule towards and against the internally tapered portion of the nut, and further pushing the first end of the ferrule tip towards and against the second end of the ferrule, thereby providing a fitting assembly providing a leak proof seal between the tubing and the port, component or fitting of the LC or other AI system.

In certain embodiments, the nut, the ferrule, and/or the ferrule tip comprises a polymer, in certain instances a biocompatible polymer such as polyetheretherketone or other biocompatible polymer. In other instances, the polymer comprises about 10%, about 15%, about 20%, about 25%, about 30%, about 35% or about 40% by weight carbon filled polyetheretherketone. In other embodiments, the nut, the ferrule, and/or the ferrule tip comprise a metal, including, but not limited to, stainless steel, such as 316 stainless steel. In further embodiments, at least one of the nut, ferrule, and ferrule tip comprise a polymer, such as polyetheretherketone, and at least one of the nut, ferrule, and ferrule tip comprise a metal, such as stainless steel.

In particular embodiments the first externally tapered end of the ferrule comprises a plurality of fingers or members that define a plurality of slots. In certain embodiments the fingers or members and the slots extend into the middle portion of the ferrule. The slots are adapted to reduce circumferential stress and place the fingers or members into bending stress to engage tubing placed through the fitting assembly. This allows direct compressive loading to load the finger or member over a large area on the tubing, which keeps the stress on the tube wall low and allows the ferrule to hold the tubing with friction force, thereby reducing biting into the tubing at the end of the finger or member. This extends the life of the tubing, allowing it to be reused multiple times with minimal or no reduction in performance. In further embodiments at least a portion of the passageway through the nut, the ferrule, and/or the ferrule tip is at least partially coated to increase the friction force on the tubing. Coatings contemplated for use with the present fitting assemblies include, but are not limited to, nickel, silica carbide, copper or diamond coating, or any combination thereof.

The present disclosure also provides an ultra high pressure liquid chromatography or other LC or AI system comprising at least one fitting assembly having a nut having a first end and a second end, and having a passageway therethrough, wherein the passageway has an internally tapered portion and a lip proximal to the second end of the nut, and wherein the second end of the nut has an externally threaded portion, a ferrule having a first externally tapered end and a second end and having a passageway therethrough, wherein the first externally tapered end of the ferrule is adapted to securely engage with the tapered portion of the passageway in the nut, and a ferrule tip having a first externally tapered end, a central portion, and a second externally tapered end, wherein the first externally tapered end and the central portion define a first lip and the second externally tapered end and the central portion define a second lip, and wherein the first end of the ferrule tip is adapted to abut with the second end of the ferrule within the passageway of the nut. Liquid chromatography and analytical instrument systems that can be used in conjunction with the presently described fitting assemblies include, but are not limited to, high pressure or high performance liquid chromatography systems, ultra high pressure or ultra high performance liquid chromatography systems, mass spectrometry systems, microflow chromatography systems, nanoflow chromatography systems, nano-scale liquid chromatography systems, capillary electrophoresis systems, reverse-phase gradient chromatography systems, or any and all combinations thereof.

These and other embodiments and advantages of the disclosed fitting assembly are described below.

DETAILED DESCRIPTION

Figure 1:
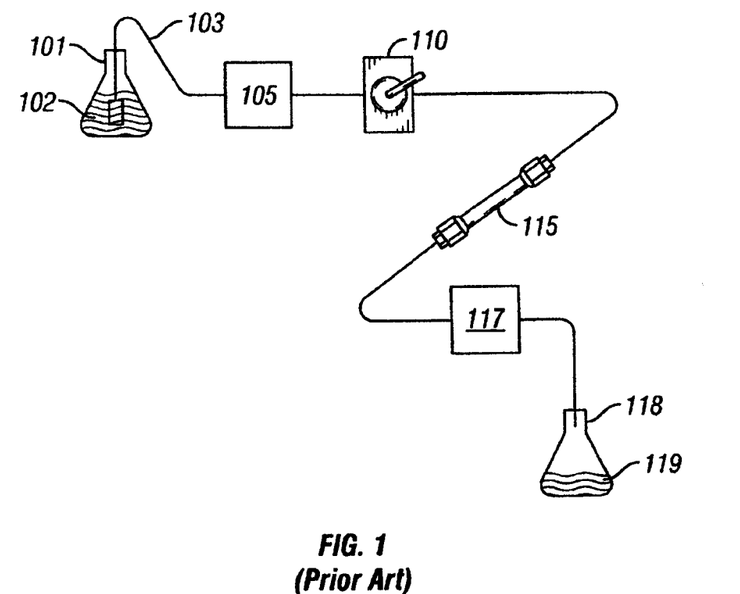
FIG. 1 is a block diagram of a conventional liquid chromatography system.

In FIG. 1, a block diagram of the essential elements of a conventional liquid chromatography (LC) system is provided. A reservoir 101 contains a solvent or mobile phase 102. Tubing 103 connects the mobile phase 102 in the reservoir 101 to a pump 105. The pump 105 is connected to a sample injection valve 110 which, in turn, is connected via tubing to a first end of a guard column (not shown). The second end of the guard column (not shown) is in turn connected to the first end of a primary column 115. The second end of the primary column 115 is then connected via tubing to a detector 117. After passing through the detector 117, the mobile phase 102 and the sample injected via injection valve 110 are expended into a second reservoir 118, which contains the chemical waste 119. As noted above, the sample injection valve 110 is used to inject a sample of a material to be studied into the LC system. The mobile phase 102 flows through the tubing 103 which is used to connect the various elements of the LC system together.

When the sample is injected via sample injection valve 110 in the LC system, the sample is carried by the mobile phase through the tubing into the column 115. As is well known in the art, the column 115 contains a packing material which acts to separate the constituent elements of the sample. After exiting the column 115, the sample (as separated via the column 115) then is carried to and enters a detector 117, which detects the presence or absence of various chemicals. The information obtained by the detector 117 can then be stored and used by an operator of the LC system to determine the constituent elements of the sample injected into the LC system. Those skilled in the art will appreciate that FIG. 1 and the foregoing discussion provide only a brief overview of a simplistic LC system that is conventional and well known in the art, as is shown and described in U.S. Pat. No. 5,472,598, issued Dec. 5, 1995 to Schick, which is hereby incorporated by reference as if fully set forth herein. Those skilled in the art will also appreciate that while the discussion herein focuses on a LC system, other analytical systems can be used in connection with various embodiments of the invention, such as a mass spectrometry, microflow chromatography, nanoflow chromatography, nano-scale liquid chromatography, capillary electrophoresis, or reverse-phase gradient chromatography system.

Preferably, for an LC system to be biocompatible, the various components (except where otherwise noted) that may come into contact with the effluent or sample to be analyzed are made of the synthetic polymer polyetheretherketone, which is commercially available under the trademark "PEEK" from Victrex. The polymer PEEK has the advantage of providing a high degree of chemical inertness and therefore biocompatibility; it is chemically inert to most of the common solvents used in LC applications, such as acetone, acetonitrile, and methanol (to name a few). PEEK also can be machined by standard machining techniques to provide smooth surfaces. Those skilled in the art will appreciate that other polymers may be desirable in certain applications.

Figure 2:
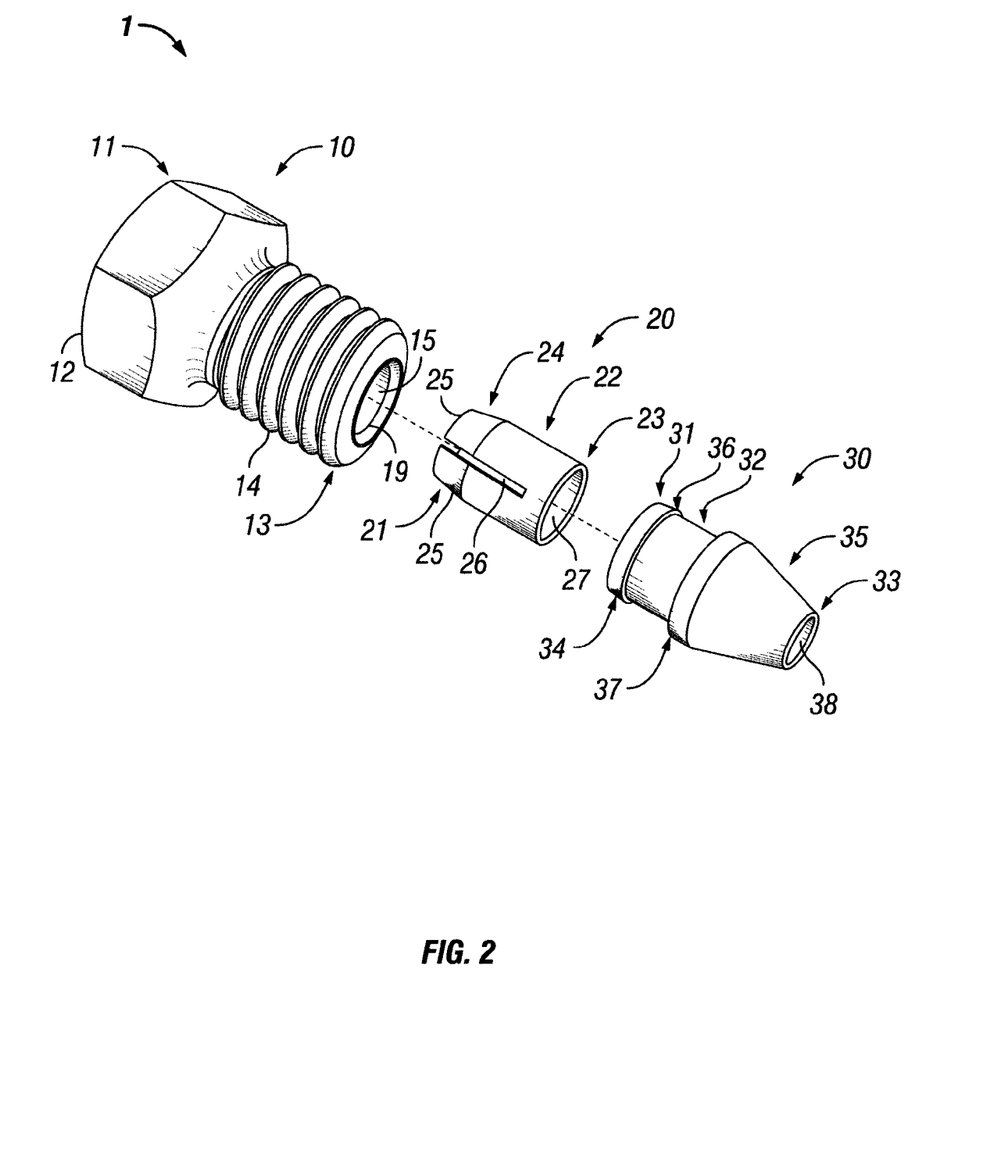
FIG. 2 is an exploded view of various components of an embodiment of a fitting assembly in accordance with one aspect of the present invention.

Referring now to FIG. 2, a first embodiment of a fitting assembly 1 is shown. As shown in FIG. 2, the assembly 1 includes a nut 10, a ferrule 20, and a ferrule tip 30. The first end 11 of the nut 10 includes the nut head 12. The other or second end 13 of the nut 10 includes an externally threaded portion 14. Passageway 15 through nut 10 is also shown as is lip 19. As detailed below, passageway 15 and lip 19 are adapted to receive and securely hold a combination of the ferrule 20 and a first end of the ferrule tip 30. As shown in FIG. 2, each of nut 10, ferrule 20, and ferrule 30 are preferably circular and symmetric about a center axis. Those skilled in the art will realize that a circular shape has advantages, but the outer diameters in particular of nut head 12 may have a non-circular shape if desired, such as having flat or concave surface portions, to allow an operator to more easily grip and rotate nut 10. As detailed herein, the externally threaded portion 14 of the nut 10 is adapted to be removably secured to a corresponding threaded portion of a port, a fitting, or a component of an LC or other analytical instrument (AI) system (not shown). Those skilled in the art will appreciate that the externally threaded portion 14 of the nut 10 may be adapted so that it can be removably engaged with any sized port, fitting, or component of an LC or other AI system (not shown). The use of external threads on one element, such as the nut 10, versus internal threads, is a matter of selection. Those skilled in the art will therefore appreciate that the nut 10 in an alternative embodiment could have internal threads (not shown) located near a second end which could be engaged with external threads (not shown) located near the first end of an alternative embodiment of a port, fitting, or component of an LC or AI system (not shown).

Still referring to FIG. 2, it can be seen that the ferrule 20 as shown has three relatively distinct portions. These include a first end 21, a middle portion 22, and a second end 23. First end 21 has a tapered portion 24 of the outer diameter so that the tapered portion 24 forms a truncated conical shape. As shown in FIG. 2, the tapered portion 24 of the first end 21 defines an angle from the axis of the ferrule 20. However, those skilled in the art will appreciate that the tapered portion 24 can define a different angle if desired. As detailed below, the tapered portion 24 of the first end 21 is adapted to be removably received in an internally tapered portion of passageway 15 of nut 10. Also shown is this embodiment of ferrule 20 are fingers or members 25, which define a slot 26 through the tapered portion 24 of the first end 21 and the middle portion 22 of the ferrule 20. Although only two fingers or members 25 are visible in FIG. 2, ferrule 20 can comprise a plurality of fingers or members, which in turn define a plurality of slots, which can extend any distance through the ferrule 20 from the first end portion 21 up to but not including the second end 23 of the ferrule 20. Passageway 27 through ferrule 20 is also shown.

Still referring to FIG. 2, it can be seen that the ferrule tip 30 as shown also has three relatively distinct portions. Ferrule tip 30 includes a first end 31, a middle portion 32, and a second end 33. In this embodiment the first end 31 and second end 33 include first and second tapered portions 34 and 35, respectively, on the outer diameter of the ferrule tip 30 that are shaped as a truncated cone. First and second tapered portions 34 and 35 extend above the middle portion 32 of the ferrule tip 30, thereby forming first and second lips 36 and 37, respectively. As detailed below, the first end 31 of the ferrule tip 30 is adapted to abut the second end of ferrule 20 within the passageway 15 of the nut 10, and first lip 36 is adapted to be removably received in the passageway 15 of the nut 10. Passageway 38 through ferrule tip 30 is also shown. In general, we believe that the externally threaded portion 14 of the nut 10 and shape and size of the second tapered portion 35 of the ferrule tip 30 should be of a shape and size so that assembled fitting assembly 1 may be easily secured to a port, fitting, or component of a LC or AI system (not shown) and may also be easily removed there from, in either case by rotating the nut head 12 (and thereby fitting assembly 1) relative to the port, fitting, or component.

Generally, the rotational force or torque applied to connect to the nut 10, ferrule 20, ferrule tip 30 and tubing extending therethrough (not shown) to a port, fitting, or component in an LC or AI system accomplishes two major tasks. First, the force of the connection of the fitting assembly 1 needs to be sufficient to provide a sealed and leak proof connection to the port, fitting, or component. In addition, the force of the connection of the fitting assembly 1 needs to be sufficient so that the tubing is securely held and is sufficient to prevent detachment due to the hydraulic force of the fluid moving through the tubing. We believe that the latter function typically involves greater forces than the former. We believe that the fitting assembly 1 (such as shown in FIG. 2) provides an advantage in that it allows for better connections at higher pressures without requiring higher forces to connect fitting assembly 1.

Figure 3:
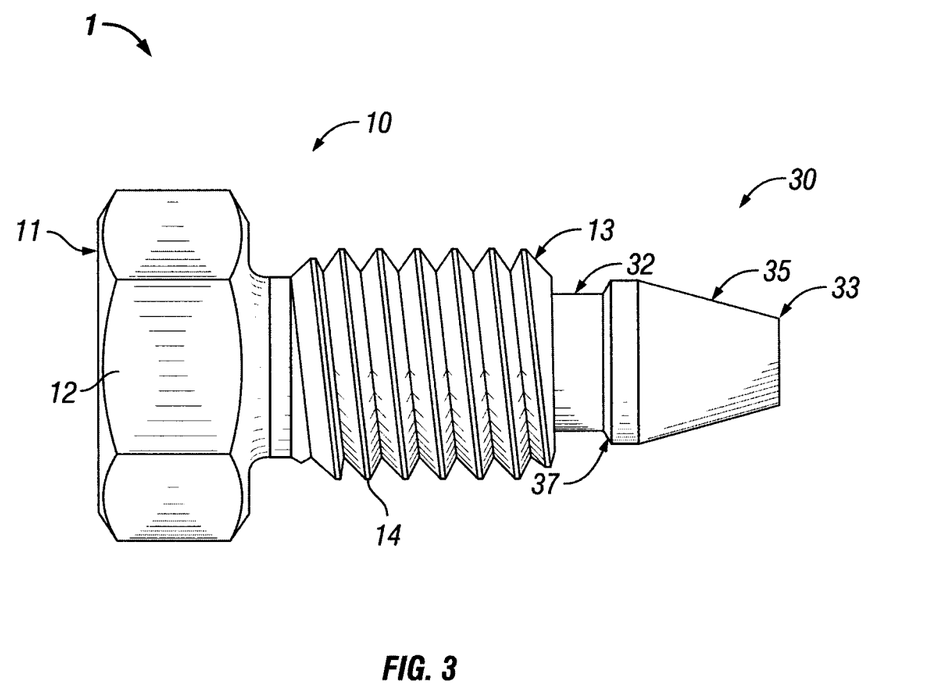
FIG. 3 is a side view of the fitting assembly of FIG. 2 when assembled.

FIG. 3 shows the fitting assembly 1 shown in FIG. 2 upon assembly by an operator. Like features and elements in the drawings have the same numerals in the various figures. Upon assembly of fitting assembly 1 only nut 10 and ferrule tip 30 are visible, as ferrule 20 (not visible) is positioned within the passageway 15 (not visible) of nut 10. Additionally, it can be seen that the first tapered portion 34 and first lip 36 of the first end 31 of the ferrule tip 30 are also not visible, as these elements are also positioned within the passageway 15 (not visible) of nut 10. Still visible upon assembly of the fitting assembly 1 are first end 11, second end 13, nut head 12, and externally threaded portion 14 of the nut 10, and middle portion 32, second end 33, second tapered portion 35, and second lip 37 of the ferrule tip 30. The passageways 15, 27, and 38 of the nut 10, ferrule 20, and ferrule tip 30 (not visible) are adapted to allow tubing (not shown) to extend through each of nut 10, ferrule 20, and fitting 30, and thus through the fitting assembly 1.

Figure 4:
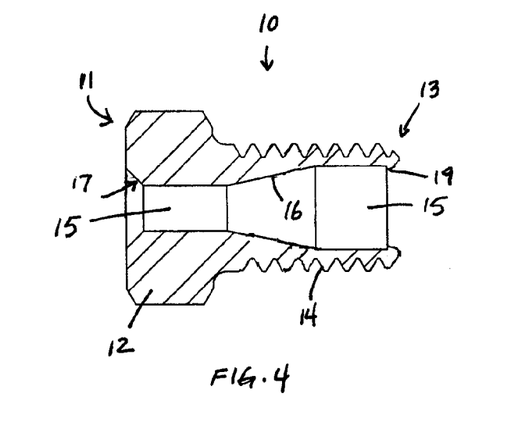
FIG. 4 is a cross-sectional view of the nut of FIG. 2.

Additional details of the cross-section of the nut 10 are shown in FIG. 4. Nut 10 has a first end 11, a nut head 12, a second end 13, and an externally threaded portion 14. Passageway 15 extends through nut 10 and includes an internally tapered portion 16. The internally tapered portion 16 of the nut 10 is adapted to receive and securely hold the tapered portion 24 of the first end portion 21 of the ferrule 20 when the fitting assembly 1 is assembled. As shown in FIG. 4, the externally threaded portion 14 forms a lip 19 near the second end 13 of the nut 10. The externally threaded portion 14 of the nut 10 is adapted to be removably secured to a corresponding threaded portion of a port, a fitting, or a component of an LC or other analytical instrument (AI) system (not shown). Also shown in FIG. 4 is an optional internally tapered portion 17 near the first end 11 of the nut 10.

Figure 5:
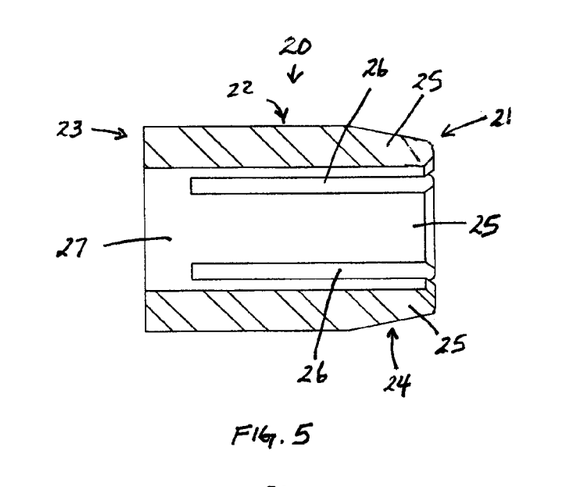
FIG. 5 is a cross-sectional view of the ferrule of FIG. 2.

Additional details of the cross-section of the ferrule 20 are shown in FIG. 5. The ferrule 20 has a first end 21 with an externally tapered portion 24, a middle portion 22 which, as shown in FIG. 5, is not tapered, and a second end 23. Although not shown, it will be appreciated that the angle of the tapered portion 24 from the axis of ferrule 20 may differ from the angle defined by the internally tapered portion 16 of the nut 10. For example, the angle defined by the tapered portion 24 of the ferrule 20 may be greater than the angle defined by the internally tapered portion 16 of the nut 10, to make it easier to obtain sufficient tubing retention with fitting assembly 1 when nut 10, ferrule 20, and ferrule tip 30 are engaged and assembled. As detailed above, the tapered portion 24 of the first end 21 of ferrule 20 is adapted to be removably received in the internally tapered portion 16 of passageway 15 of nut 10. Shown in greater detail in FIG. 5 are members 25, which define slots 26 through the tapered portion 24 of the first end 21 and the middle portion 22 of the ferrule 20. It will be appreciated by the skilled artisan that the slots 26 can extend any distance through the ferrule 20 from the first end portion 21 up to but not including the second end portion 23 of the ferrule 20. As shown in FIG. 5, the passageway 27 through ferrule 20 is not tapered.

Figure 6:
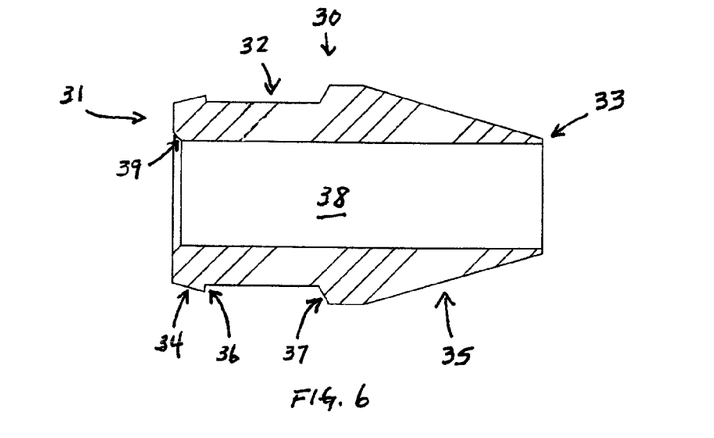
FIG. 6 is a cross-sectional view of a 45° rotation of the ferrule tip of FIG. 2.

Additional details of the cross-section of the ferrule tip 30 are shown in FIG. 6. The ferrule tip 30 has a first end 31, a middle portion 32, and a second end 33, and further has an externally tapered portion 34 at the first end 31 and an externally tapered portion 35 at the second end 33 of the ferrule tip 30. As shown in FIG. 6, the externally tapered portions 34 and 35 extend further from the central axis of the ferrule tip 30 than the middle portion 32, thereby defining a first lip 36 and a second lip 37, respectively, and the externally tapered portion 34 at the first end 31 of the ferrule tip 30 is tapered in the opposite direction compared to the externally tapered portion 35 at the second end 33 of the ferrule tip 30. The first end 31 of the ferrule 30 is adapted to abut the second end 23 of the ferrule 20 when the fitting assembly 1 is assembled. In addition, the first lip 36 is adapted to be securely retained by lip 19 in passageway 15 of the nut 10 when the fitting assembly 1 is assembled. Also shown in FIG. 6 is passageway 38 extending through the ferrule tip 30, with an optional internally tapered portion 39 near the first end 31.

It will be appreciated that the nut 10, ferrule 20, and ferrule tip 30 can comprise a number of different materials. For example, each of nut 10, ferrule 20 and ferrule tip 30 in an fitting assembly 1 can comprise a metal, such as stainless steel, or each can comprise a different material, such as a polymer. For example, the fitting assembly 1 can comprise a nut 10 comprising polyetheretherketone (PEEK), a ferrule 20 comprising stainless steel, and a ferrule tip 30 comprising PEEK. It will be appreciated that a variety of metals and polymers may be selected for any one or more of nut 10, ferrule 20, and ferrule tip 30 depending on the particular application, as that may involve a particular type of sample, a particular type of solvent, and/or a particular pressure range. In addition, the selection of materials for the tubing may lead to a selection of a particular material for nut 10, ferrule 20, and/or ferrule tip 30. In addition, PEEK (or other polymers) may be used that is reinforced with carbon, carbon fibers or steel fibers, or the like. Other polymer materials which may be used include, but are not limited to, TEFLON®, TEFZEL®, DELRIN®, polyphenylene sulfide (PPS), polypropylene, and others, depending on the foregoing factors and perhaps others, such as cost. Those skilled in the art will further appreciate that fitting assembly 1 is shown as a fitting connection for connecting tubing to another component in an LC or other AI system, and that the other component may be any one of wide variety of components. Such components include pumps, columns, filters, guard columns, injection valves and other valves, detectors, pressure regulators, reservoirs, and other fittings, such as unions, tees, crosses, adapters, splitters, sample loops, connectors, and the like.

In order for a fitting assembly to seal, it should generally remain in compression (relative to the conical surface of the port) throughout all environmental conditions. Therefore, in certain aspects a coating with a high coefficient of friction between the outer surface of the tube material is applied to at least a portion of the internal bore surface of the described fitting assembly 1. The high coefficient of friction between the outer surface of the tube and the internal bore surface of the fitting connection or assembly 1 keeps the tube from extruding out of the port during pressurization, which results in dramatically increased burst pressure. In such embodiments the fitting connection or assembly is coated at the internal bore surface that contacts the tube starting at approximately 0.005 inches, about 0.0075 inches, about 0.01 inches, or about 0.02 inches from the tip. Coatings suitable for use with the presently described fitting connection or assembly include, but are not limited to, nickel, silica carbide, copper, and diamond coatings, and combinations thereof.

Methods of using the fitting assembly 1 (such as shown in FIG. 2 and FIG. 3) are now described in further detail. An operator can first provide a nut 10, ferrule 20 and ferrule tip 30, as well as tubing (not shown). In one approach, the operator can insert a portion of the tubing through the passageways 15, 27, and 38 of nut 10, ferrule 20 and ferrule tip 30, respectively, in that order without assembling or otherwise connecting any of nut 10, ferrule 20 and ferrule tip 30. Next, the operator can insert the ferrule 20 into the passageway 15 in the second end 13 of the nut 10, and the insert the first end 31 of the ferrule tip 30 into the passageway 15 in the nut 10, such that the first end 31 of the ferrule tip 30 abuts the second end 23 of the ferrule 20 and pushes the first end 21 of the ferrule 20 against the internal tapered portion 16 of the passageway 15 of the nut 10, and the first lip 34 of the ferrule tip 30 is retained within the passageway 15 of the nut 10 by lip 19. The operator can then engage the externally threaded portion 14 of the nut 10 with the internally threaded portion of a port, fitting, or component of a LC or AI system (not shown). Once the externally threaded portion 14 of the nut 10 and the internally threaded portion of the port, fitting, or component of a LC or AI system begin to mate or engage, the operator then rotates the nut head 12 of the fitting assembly 1 relative to the port, fitting, or component of a LC or AI system, rotates the port, fitting, or component of a LC or AI system relative to the nut head 12 of the fitting assembly 1, or rotates both the nut head 12 of the fitting assembly 1 and the port, fitting, or component of a LC or AI system relative to each other. By so rotating the nut head 12 of the fitting assembly 1 and the port, fitting, or component of a LC or AI system relative to one another, the operator drives the ferrule 20 and ferrule tip 30 further into the interior passageway 15 of the nut 10. In doing so, the operator thus forces the first end 21 of the ferrule 20 against the internally tapered portion 16 of the passageway 15 of nut 10 and also forces the externally tapered portion 34 of the first end of ferrule tip 30 into the passageway 15 of the nut 10, thus engaging the first lip 36 of the ferrule tip 30 with the lip 19 of the passageway 15 of the nut 10. In doing so, the externally tapered first end 24 of the ferrule 20 is compressed and held firmly against the internally tapered portion 16 of the passageway 15 of the nut 10, thereby forming a leak proof connection. Because the first ends 24 of the ferrule 20 may be deformed or compressed as it is forced against the tapered portion 16 of the passageway 15 of the nut 10, a leak proof connection may be obtained by the operator without the use of additional tools such as a wrench, pliers or the like. Alternatively, fitting assembly 1 can be provided to the operator pre-assembled. In one specific embodiment, when tubing having an outer diameter of 0.0625 inches is used, the minimum diameter of the passageway in the fitting assembly can range between about 0.065 and about 0.067 inches.

To disconnect a fitting assembly 1, such as shown in FIG. 2 and FIG. 3, an operator may either rotate the fitting assembly 1 relative to the port, fitting, or component of a LC or AI system (not shown), rotate the port, fitting, or component of a LC or AI system relative to the fitting assembly 1, or rotate both the port, fitting, or component of a LC or AI system and the fitting assembly 1 relative to each other. By rotating the port, fitting, or component of a LC or AI system and/or the fitting assembly 1 relative to one another, the operator thus rotates the externally threaded portion 14 of nut 10 and the internally threaded portion of the port, fitting, or component of a LC or AI system, respectively, and thereby disengages the connection between such threaded portions. At this point, the operator can use the assembly 1 and the leak proof connection it provides, until the operator decides to remove the tubing (not shown) from the assembly 1. By selecting the direction of the threading of the externally threaded portion 14 of the nut 10 and internally threaded portion of the port, fitting, or component of a LC or AI system, respectively, the operator can turn the entire fitting assembly 1 (when connected) by turning or rotating nut 10, such that the fitting assembly 1 rotates relative to the port, fitting, or component of a LC or AI system (not shown) and disengages therefrom. Thus, the entire fitting assembly 1 is easily disconnected from the port, fitting, or component of a LC or AI system (not shown).

Figure 7:
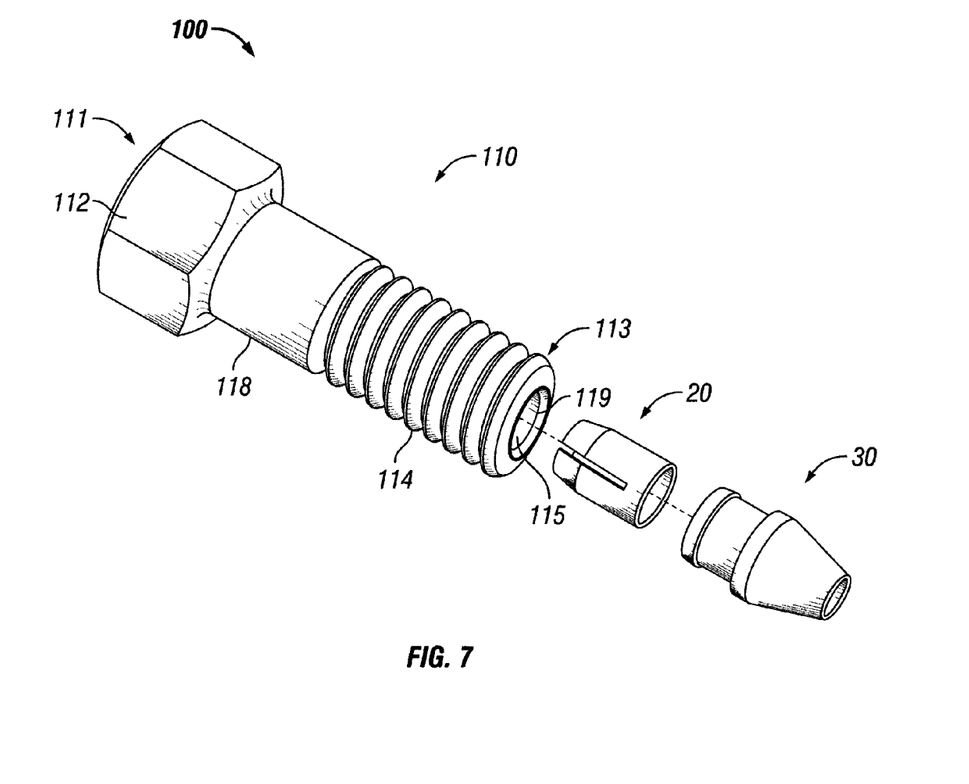
FIG. 7 is an exploded view of various components of an alternate embodiment of a fitting assembly in accordance with one aspect of the present invention.

Referring now to FIG. 7, an alternative embodiment of a fitting assembly 100 is illustrated. Like the assembly 1 of FIG. 2, the assembly 100 of FIG. 7 includes a ferrule 20 and a ferrule tip 30, each of which has the same features as previously described. However, in this embodiment, nut 110 includes a non-threaded portion 118 near the first end 111 and the nut head 112. As before, the other or second end 113 of the nut 110 includes an externally threaded portion 114, and passageway 115 through nut 110 and lip 119 are also shown. As detailed above, passageway 115 and lip 119 are adapted to receive and securely hold a combination of the ferrule 20 and a first end of the ferrule tip 30. As shown in FIG. 7, each of nut 110, ferrule 20, and ferrule 30 are generally circular and symmetric about a center axis. Those skilled in the art will realize that a circular shape has advantages, but the outer diameters in particular of nut head 112 may have a non-circular shape if desired, such as flat or concave portions, to allow an operator to easily grip and rotate nut 110. As detailed herein, the externally threaded portion 114 of the nut 110 is adapted to be removably secured to a corresponding threaded portion of a port, a fitting, or a component of an LC or other analytical instrument (AI) system (not shown). Those skilled in the art will appreciate that the externally threaded portion 114 of the nut 110 may be adapted so that it can be removably engaged with any sized port, fitting, or component of an LC or other AI system (not shown). The use of external threads on one element, such as the nut 110, versus internal threads, is a matter of selection. Those skilled in the art will therefore appreciate that the nut 110 in an alternative embodiment could have internal threads (not shown) located near a second end which could be engaged with external threads (not shown) located near the first end of an alternative embodiment of a port, fitting, or component of an LC or AI system (not shown).

Figure 8:
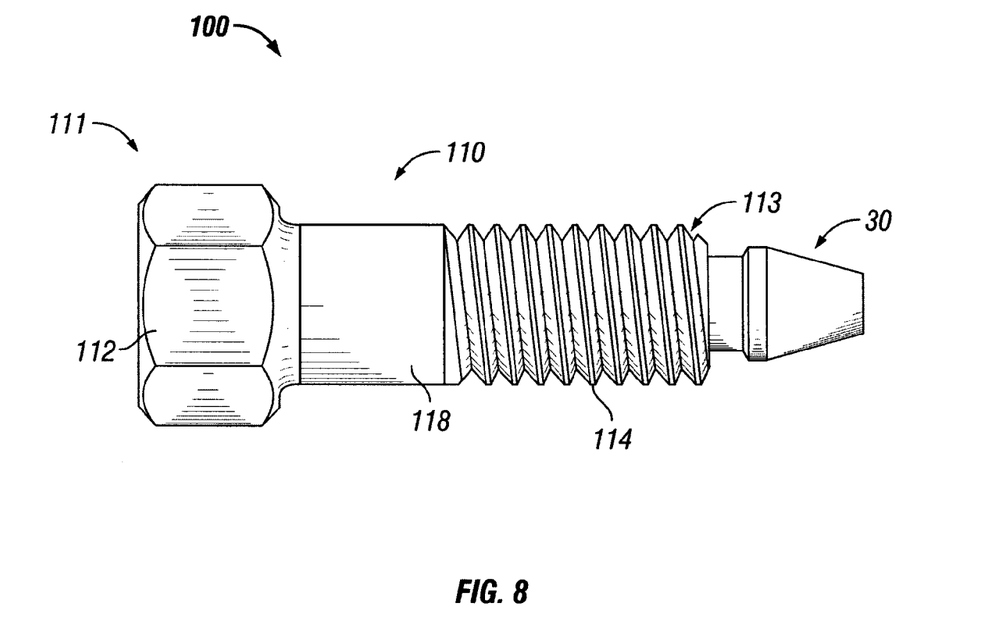
FIG. 8 is a side view of the alternative embodiment of the fitting assembly of FIG. 7 when assembled.

FIG. 8 shows the alternative embodiment of the fitting assembly 100 shown in FIG. 7 upon assembly by an operator. Like features and elements in the drawings have the same numerals in the various figures. Upon assembly of fitting assembly 100 only nut 110 and ferrule tip 30 are visible, as ferrule 20 (not visible) is positioned within the passageway 115 (not visible) of nut 110. Additionally, it can be seen that the first tapered portion 34 and first lip 36 of the first end 31 of the ferrule tip 30 are also not visible, as these elements are also positioned within the passageway 115 (not visible) of nut 110. Still visible upon assembly of the fitting assembly 100 are first end 111, second end 113, nut head 112, non-threaded portion 118, and externally threaded portion 114 of the nut 110, and middle portion 32, second end 33, second tapered portion 35, and second lip 37 of the ferrule tip 30. The passageways 115, 27, and 38 of the nut 110, ferrule 20, and ferrule tip 30 (not visible) are adapted to allow tubing (not shown) to extend through each of nut 110, ferrule 20, and fitting 30, and thus through the fitting assembly 100.

The following example is included to demonstrate preferred embodiments of the invention. It should be appreciated by those of skill in the art that the techniques disclosed in the example which follows represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention. The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein, will become apparent to those skilled in the art from the foregoing description. Such modifications are intended to fall within the scope of the appended claims.

Performance of a fitting assembly 1 as described herein, for example as shown in FIG. 2, was tested as detailed below. In the tested fitting assembly 1, the ferrule 20 and the ferrule tip 30 are captivated, yet free to rotate and actuate independently. This allows the ferrule tip 30 to serve as the fluidic seal and is independent of the ferrule 20, which locks the tube in place. When the nut 10 is tightened the ferrule 20 and the ferrule tip 30 are compressed between the nut 10 and the port. Initially, the ferrule 20 transfers thrust (axial force from screwing the nut 10 into the port) into the ferrule tip 30, by closing the clearances between the port, the ferrule tip 30, the ferrule 20 and the nut 10. Also, during this initial tightening, the fingers 25 of the ferrule 20 are easily forced against the tube (to a certain degree), since they are, by design, slotted and therefore have relatively little strength to resist this. As more torque is applied to the nut 10, the ferrule tip 30 and the ferrule 20 and fingers 25 act like springs in the sense that they compress and store energy. Friction is generated between the ferrule tip 30 and port, the ferrule tip 30 and tube, between the ferrule tip 30 and the ferrule 20, between the fingers 25 and the tube, and between the fingers 25 and the nut 10. In the present fitting assemblies the additional torque applied to the nut 10 is transferred first to friction interfaces at the ferrule 20, and then to the friction surfaces at the ferrule tip 30. This means that more energy from nut torque goes into the ferrule fingers 25 (to hold the tube) than the ferrule tip 30 (for sealing the fitting). It is believed that in fittings such as this, the energy required to seal the ferrule tip is less than the energy required to securably retain the tube.

The fingers 25 are designed and adapted to apply a high enough normal force over a large enough surface area to keep the tube from moving while the fitting assembly 1 is used in service (e.g., when pressure is applied to fluid in the tube once connected in a LC or other AI system), and to keep the tube from being point loaded or permanently deformed by the fingers. In other words, the fingers 25 apply a radial force on the tube without point loading (as is the case with previous fitting assembly designs), which would leave a sharp mark (an annular groove) that is sometimes visible to the naked eye, and that essentially locks the ferrule and tube together placing them into a shear condition (e.g., in the same situation as if there were a threaded connection). While conventional fitting assemblies may hold the tube quite well, this condition forces the tube to only be used in the port to which it was initially connected (e.g., the port in which deformation occurred), because each port varies slightly due to manufacturing tolerances, and a previously deformed tube with a groove could easily shift out of another port if so connected because the ferrule would likely be essentially guided into the pre-existing groove. This is undesirable because, among other things, such a condition likely adds dead volume to the connection and the LC or AI system. Unlike conventional fittings where such deformation is a problem, in the fitting assembly 1 of this example, there may be deformation (especially when over-tightened on multiple uses), but we have found that any such deformation is not in the form of a sharp annular groove in the tube and does not prevent further use of the fitting assembly 1.

In the presently described fitting assembly 1, the ferrule fingers 25 are designed and adapted to deflect radially with minimal force. The finger material, length, thickness, and quantity are designed and adapted to allow for the appropriate stiffness to enable the fingers 25 to function as desired and described. As the internally tapered portion 16 of the nut 10 is forced over the tapered surface of the fingers 25 during the formation of a connection, the fingers 25 easily deflect until the tube is contacted over a relatively large surface area, without permanently deforming the fingers 25 at their base (e.g., where the fingers contact the tube). Continued force places the fingers 25 into compressive loading, which allows the fingers 25 to securely grip the tube. The spring-like action of the fingers 25 also allow the ferrule 20 to provide a slight radial force on tubes within a specific outside diameter tolerance (i.e., a ferrule 20 can be placed on a tube with an outer diameter of 0.063 inches or 0.064 inches and lightly grip the tube). This design feature allows the ferrule 20 to remain on a tube without falling off, yet is still easily positioned on the tube by the hand by the operator. Loading over a relatively large area as described also keeps the inner wall of the tube from collapsing in a specific area and creating a flow restriction. Such flow restrictions may lead to turbulent flow and are considered undesirable.

The interface of the tapered portion 24 of the ferrule 20 to the internally tapered portion 16 of the nut 10 is designed and adapted to allow the nut 10 to provide maximum radial force without locking the two tapers together. In this example, each taper is designed to be from about 18 to about 28° included angle with an about 1 to about 5° mismatch between the tapers (e.g., the tapers are mismatched so that the area at the extreme end of the finger 25 contacts the internally tapered portion 16 of the nut 10 first). This exemplary design keeps the parts from locking, yet allows the fingers to be loaded and deflected without causing permanent deformation to the fingers 25, nut 10, or tube that prevents re-use of the fitting assembly 1. In most of the applications of the fitting assembly 1, no marks visible to the naked eye are made on the tube by the fingers 25. These ferrule tapers are also designed and adapted so that the natural tendency of the tube towards backing out of the port during pressurization of the fluid in the LC or AI system further presses the fingers 25 against the surface of the tube, thus increasing the normal force and therefore increasing the frictional force restraining the tube. The fitting in this example is also designed and adapted to retain the tubing in the fitting during over-pressurization and vent the pressure without having the tubing extrude entirely from the fitting to prevent harm to the operator.

In testing of assemblies like those shown and described herein, good results have been obtained. In a first series of tests, assemblies like those shown in FIG. 2 were assembled, in which the tubing was made of stainless steel, the nut 10 and ferrule 20 were made of stainless steel, while the ferrule tip 30 was made of PEEK (30% (by weight) carbon filled). The first two tests were conducted using a zero dead volume (ZDV) union (U-438; commercially available from IDEX Health and Science, Oak Harbor, Wash.). In the first test, we used a torque wrench manufactured and available from Tohnichi, model 20STC-A, to measure the torque used to seal the test fitting assemblies. It was determined that the fitting assembly was able to seal with as little as about 2.0 inch-pounds of torque, while the maximum torque that the fitting assembly was capable of withstanding prior to physical damage to the tapered end of the ferrule was about 14 inch-pounds. Above 14 inch-pounds of torque or so the tapered end of the stainless steel collet ferrule collapsed, making multiple assembly cycles impossible. The second test measured burst pressure versus assembly torque, and showed that burst pressure increased from approximately 10,000 psi to approximately 32,500 psi as torque increased from about 2.0 inch-pounds to about 12.0 inch-pounds. In the third test, a standard union (U-411; commercially available from IDEX Health and Science) was used, as this was determined to be more representative of actual use of the fitting assembly. Using about 9.5 inch-pounds of torque to seal the fitting assembly, the minimum burst pressure was determined to be about 39,331 psi, with an average of about 43,466 psi.

While the present invention has been shown and described in various embodiments, those skilled in the art will appreciate from the drawings and the foregoing discussion that various changes, modifications, and variations may be made without departing from the spirit and scope of the invention as set forth in the claims. Hence the embodiments shown and described in the drawings and the above discussion are merely illustrative and do not limit the scope of the invention as defined in the claims herein. The embodiments and specific forms, materials, and the like are merely illustrative and do not limit the scope of the invention or the claims herein.

We claim:

1. A fitting assembly for use in a liquid chromatography system, comprising:
  a) a nut having a first end and a second end, and having a passageway therethrough, wherein said passageway has an internally tapered portion and a lip proximal said second end of said nut, and wherein said second end of said nut has an externally threaded portion;
  b) a ferrule having a first externally tapered end and a second end and having a passageway therethrough, wherein said first externally tapered end of said ferrule is adapted to securely engage with said tapered portion of said passageway in said nut; and
  c) a ferrule tip having a first externally tapered end, a central portion, and a second externally tapered end, and having a passageway therethrough, wherein said first externally tapered end and said central portion define a first lip and said second externally tapered end and said central portion define a second lip, and wherein said first end of said ferrule tip is adapted to abut with said second end of said ferrule within said passageway of said nut, and said first lip of said ferrule tip securely engages said lip of said nut.

2. The fitting assembly according to claim 1, wherein said first externally tapered end of said ferrule comprises a plurality of members.

3. The fitting assembly according to claim 1, wherein said ferrule and said ferrule tip may rotate independently.

4. The fitting assembly according to claim 1, wherein said ferrule and said ferrule tip may actuate independently.

5. The fitting assembly according to claim 1, wherein at least a portion of an angle of said internally tapered portion of said nut and at least a portion of an angle of said first externally tapered end of said ferrule are between about 18° and about 28° included angle, and the angles of said portions of said internally tapered portion of said nut and said first externally tapered end of said ferrule differ by about 1° to about 5°.

6. The fitting assembly according to claim 1, wherein said nut, said ferrule, or said ferrule tip comprises a polymer.

7. The fitting assembly according to claim 6, wherein said polymer comprises polyetheretherketone.

8. The fitting assembly according to claim 7, wherein polymer comprises about 10% to about 30% by weight carbon filled polyetheretherketone.

9. The fitting assembly according to claim 1, wherein said nut, said ferrule, or said ferrule tip comprises a metal.

10. The fitting assembly according to claim 9, wherein said nut, said ferrule, or said ferrule tip comprises stainless steel.

11. The fitting assembly according to claim 10, wherein at least one of said nut, ferrule, and ferrule tip comprises polyetheretherketone and at least one of said nut, ferrule, and ferrule tip comprises stainless steel.

12. The fitting assembly according to claim 1, further comprising at least one tube extending through the passageways of said nut, said ferrule, and said ferrule tip.

13. The fitting assembly according to claim 1, wherein said fitting assembly consists essentially of biocompatible materials.

14. The fitting assembly according to claim 1, wherein at least a portion of said passageway through said nut, said ferrule, or said ferrule tip is at least partially coated.

15. The fitting assembly according to claim 14, wherein at least a portion of said passageway through said nut, said ferrule, and said ferrule tip is at least partially coated.

16. The fitting assembly according to claim 14, wherein at least a portion of said passageway through said nut, said ferrule, or said ferrule tip is at least partially coated with a coating comprising a nickel, silica carbide, copper or diamond coating, or a combination thereof.

17. An analytical instrument system comprising at least one fitting assembly having:
a) a nut having a first end and a second end, and having a passageway therethrough, wherein said passageway has an internally tapered portion and a lip proximal said second end of said nut, and wherein said second end of said nut has an externally threaded portion;
b) a ferrule having a first externally tapered end and a second end and having a passageway therethrough, wherein said first externally tapered end of said ferrule is adapted to securely engage with said tapered portion of said passageway in said nut; and
c) a ferrule tip having a first externally tapered end, a central portion, and a second externally tapered end, and having a passageway therethrough, wherein said first externally tapered end and said central portion define a first lip and said second externally tapered end and said central portion define a second lip, and wherein said first end of said ferrule tip is adapted to abut with said second end of said ferrule within said passageway of said nut, and said first lip of said ferrule tip securely engages said lip of said nut.

18. The system according to claim 17, wherein at least a portion of said first externally tapered end of said ferrule comprises a plurality of members.

19. The system according to claim 17, wherein said nut, said ferrule, or said ferrule tip comprises a polymer.

20. The system according to claim 17, wherein said nut, said ferrule, or said ferrule tip comprises a metal.

21. The system according to claim 17, wherein said fitting assembly consists essentially of biocompatible materials.

22. The system according to claim 17, wherein said passageway through said nut, said ferrule, or said ferrule tip is coated.

23. The system according to claim 17 wherein said analytical instrument system comprises a liquid chromatography system.

24. The system according to claim 23, wherein said analytical instrument system comprises an ultra high pressure or ultra high performance liquid chromatography system.

25. The system according to claim 17, wherein said analytical instrument system comprises a high performance or high pressure liquid chromatography system, an ultra high performance or ultra high pressure liquid chromatography system, a mass spectrometry system, a microflow chromatography system, a nanoflow chromatography system, a nanoscale chromatography system, a capillary electrophoresis system, a reverse-phase gradient chromatography system, or a combination thereof.

26. A method of connecting tubing in a liquid chromatography system comprising connecting a fitting assembly comprising a tube extending therethrough to a port, fitting or component of said liquid chromatography system;
wherein said fitting assembly comprises:
a) a nut having a first end and a second end, and having a passageway therethrough, wherein said passageway has an internally tapered portion and a lip proximal said second end of said nut, and wherein said second end of said nut has an externally threaded portion;
b) a ferrule having a first externally tapered end and a second end and having a passageway therethrough, wherein said first externally tapered end of said ferrule is adapted to securely engage with said tapered portion of said passageway in said nut; and
c) a ferrule tip having a first externally tapered end, a central portion, and a second externally tapered end, and having a passageway therethrough, wherein said first externally tapered end and said central portion define a first lip and said second externally tapered end and said central portion define a second lip, and wherein said first end of said ferrule tip is adapted to abut with said second end of said ferrule within said passageway of said nut, and said first lip of said ferrule tip securely engages said lip of said nut;
wherein said port, fitting or component comprises a first end having an internally threaded portion and an internally tapered portion, a second end and a passageway therethrough, and wherein said internally threaded portion of said fitting or component is adapted to securely engage with said externally threaded portion of said nut, and wherein the internally tapered portion of said fitting or component is adapted to receive and hold said second externally tapered end of said ferrule tip.

27. The method according to claim 26, wherein said first externally tapered end of said ferrule comprises a plurality of members.

28. The method according to claim 27, wherein said members contact said tube without substantially deforming the tube.

29. The method according to claim 26, wherein at least a portion of said passageway through said nut, said ferrule, or said ferrule tip is at least partially coated.

* * * * *